US010172587B2

(12) United States Patent
Franke et al.

(10) Patent No.: US 10,172,587 B2
(45) Date of Patent: Jan. 8, 2019

(54) PHANTOM SYSTEM, USE OF THE SYSTEM, AND IMAGING CONFIGURATION HAVING A PHANTOM SYSTEM

(71) Applicant: Bruker BioSpin MRI GmbH, Ettlingen (DE)

(72) Inventors: Jochen Franke, Karlsruhe (DE); Ulrich Heinen, Ettlingen (DE)

(73) Assignee: Bruker BioSpin MRI GmbH, Ettlingen (DE)

( * ) Notice: Subject to any disclaimer, the term of this patent is extended or adjusted under 35 U.S.C. 154(b) by 290 days.

(21) Appl. No.: 15/069,991

(22) Filed: Mar. 15, 2016

(65) Prior Publication Data
US 2016/0278735 A1    Sep. 29, 2016

(30) Foreign Application Priority Data

Mar. 24, 2015  (DE) .................. 10 2015 205 347

(51) Int. Cl.
| | |
|---|---|
| A61B 6/00 | (2006.01) |
| G01T 1/164 | (2006.01) |
| G01R 33/58 | (2006.01) |
| G01T 7/00 | (2006.01) |
| G01N 23/04 | (2018.01) |
| A61B 5/055 | (2006.01) |
| A61B 6/03 | (2006.01) |

(52) U.S. Cl.
CPC .............. *A61B 6/583* (2013.01); *A61B 5/055* (2013.01); *A61B 6/032* (2013.01); *A61B 6/037* (2013.01); *G01N 23/04* (2013.01); *G01R 33/58* (2013.01); *G01T 1/164* (2013.01); *G01T 7/00* (2013.01)

(58) Field of Classification Search
CPC ......... A61B 6/583; A61B 5/055; A61B 6/032; A61B 6/037; G01T 1/164; G01T 7/00; G01T 7/005; G01R 33/58; G01N 23/04

USPC .................. 73/866.4, 1.82, 1.83, 1.86, 1.01; 324/300, 308, 317, 321; 600/407–436
See application file for complete search history.

(56) References Cited

U.S. PATENT DOCUMENTS

| | | | |
|---|---|---|---|
| 3,263,740 A * | 8/1966 | Bruce ................. | G05D 23/275 165/108 |
| 4,692,704 A | 9/1987 | Gray | |
| 4,777,442 A | 10/1988 | Rosenthal | |
| 7,056,019 B1 | 6/2006 | Hanson | |
| 7,368,912 B2 | 5/2008 | Kreibich | |
| 8,814,572 B2 | 8/2014 | Eberler | |

OTHER PUBLICATIONS

Justin J. Konkle "Projection Reconstruction Magnetic Particle Imaging", IEEE Trans Med Imaging. Feb. 2013; 32(2): 338-347.

* cited by examiner

*Primary Examiner* — Robert R Raevis
(74) *Attorney, Agent, or Firm* — Paul Vincent

(57) ABSTRACT

A phantom system has a housing (2) with a lower part (3) having an opening in the z-direction and a cover part (4) for closing the opening of the housing (2). A first plate-shaped insert element (10*a*) has at least one depression (11*a*) for receiving a liquid substance. The lower part (3) and the cover part (4) delimit a cavity (5) with an insert area (8), which is constituted to receive the first insert element (10*a*). A first sealing element (14*a*) seals the first insert element (10*a*) against the cavity (5) and a fixing facility fixes the first insert element (10*a*) in the cavity (4) of the housing (2) in an operating state of the MPI phantom. The phantom permits good contrast in MPI, MRI, or μCT using liquid contrast media.

13 Claims, 5 Drawing Sheets

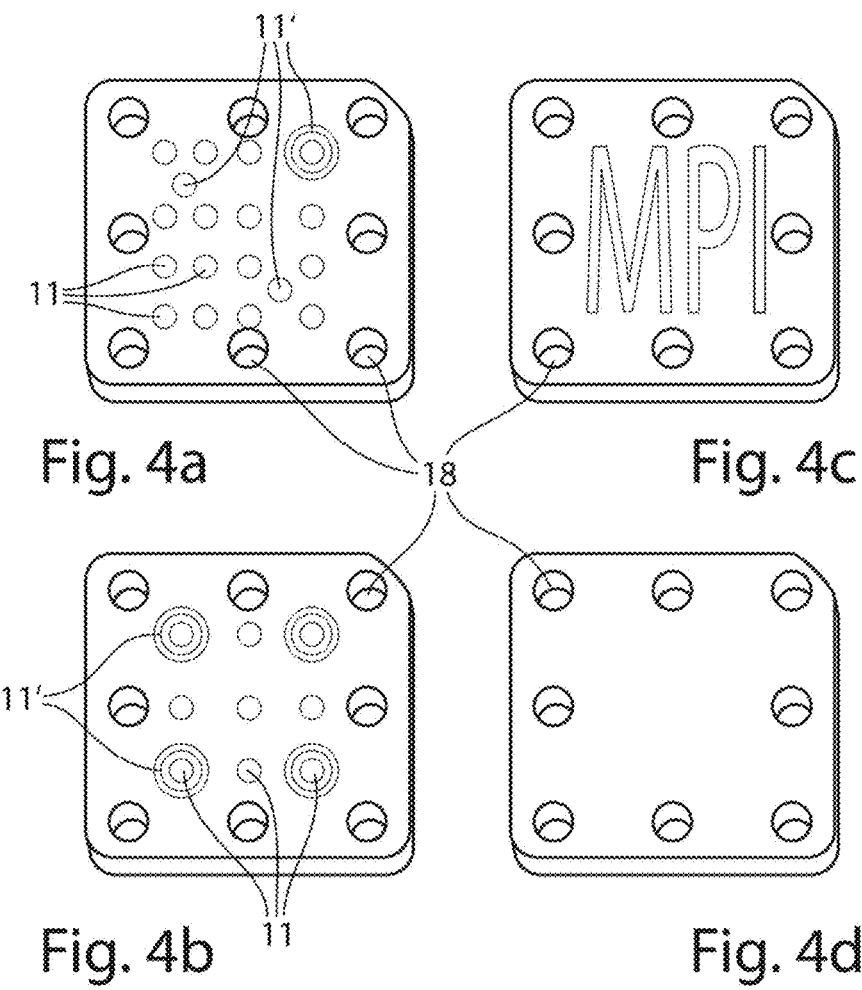

PHANTOM SYSTEM, USE OF THE SYSTEM, AND IMAGING CONFIGURATION HAVING A PHANTOM SYSTEM

This application claims Paris convention priority from DE 10 2015 205 347.4 filed on Mar. 24, 2015, the entire disclosure of which is hereby incorporated by reference.

BACKGROUND OF THE INVENTION

The invention relates to a phantom system for the calibration and/or characterization of an imaging configuration, as well as a use of the phantom system, and an imaging configuration with this phantom system.

A phantom for MRI, PET, and X-ray configurations is known, for example, from U.S. Pat. No. 7,056,019 B1.

Phantoms are established tools for the characterization and/or calibration of imaging systems with respect to spatial resolution, sensitivity, or geometrical distortion. For MPI (magnetic particle imaging) applications, in particular, the availability of standard phantoms is particularly desirable in order to simplify direct comparison among the various MPI scanner designs, which have been developed since this new imaging method has become established. Critical parameters for characterizing MPI systems are (anisotropic) spatial resolution, geometrical accuracy of the image, signal homogeneity across the image volume, and sensitivity. In order to glean valuable information about the practical use of the systems, these parameters must be tested with the same (usually liquid) contrast media, which are also used in subsequent experiments, as these can also influence those parameters, in particular, spatial resolution and sensitivity.

Until now, mainly ad hoc or makeshift phantoms were used in MPI development. One typical technology is the use of thin tubes that are filled with contrast medium and then bent into a desired spatial shape (Konkle, J. et al "Projection Reconstruction Magnetic Particle Imaging" IEEE Trans Med imaging, 2013 Feb.; 32(2); 338-347.). Other groups use conventional test vessels, which are molded into a defined spatial configuration using adhesive tape or foam-rubber matrix structures. Polyacrylic flow phantoms have also been used, through whose channels liquid containing contrast medium can be pumped. The disadvantage of ad-hoc solutions is the lack of reproducibility and transferability. The use of filled tubes restricts the design of the phantom because spatial path patterns always occur. What is more, air bubbles in the tube are difficult to eliminate. Phantoms based on polyacrylic, in particular, have the disadvantage that small volumes of aqueous contrast medium can dry up due to the absorption of water by the matrix. With such phantom configurations, it is therefore not possible to introduce liquid contrast medium into the imaging system in a well-defined spatial configuration.

Because the MPI method typically requires a second measuring method to provide a morphological reference, it is desirable to use such phantoms that also provide a good contrast in other methods such as MRI or μCT. However, the contrast media used for MPI generate black images with conventional MRI measuring sequences. With existing MPI phantom concepts, it is very difficult to place MRI-active and MPI-active image elements into a well-defined mutual spatial relationship.

U.S. Pat. No. 7,056,019 B1 discloses a phantom system for the calibration of various imaging methods, such as, for example, CT, PET, or MRI scanners. This phantom system comprises a transparent cubic housing with a central opening, in which a measuring head can be inserted. A multiplicity of small holes is provided in the housing. Different cylindrical probes can be inserted into these holes, which, due to their density, can simulate different tissue types. However, liquid contrast media cannot be used with this phantom system. The phantom system known from U.S. Pat. No. 7,056,019 B1 is therefore only of limited suitability for MPI measurements.

The object of this invention is to provide a phantom system, which, in particular with liquid contrast media, permits good contrast with various methods such as MPI, MRI, or μCT (multi-modal). Because the spatial resolution of the MPI scanner is typically anisotropic, it is furthermore desirable to permit different phantom orientations.

SUMMARY OF THE INVENTION

This object is inventively achieved by a phantom system according to the independent claim.

The inventive phantom system comprises a housing, wherein the housing has a lower part with an opening in the z-direction and a cover part for closing the opening of the housing, and a first plate-shaped insert element with at least one depression for receiving a liquid or powder substance. The lower part and the cover part delimit a cavity with an insert area, which is constituted in such a way as to receive the first insert piece. Furthermore, the inventive phantom system comprises a sealing facility with a first sealing element for the liquid-tight sealing of the first insert element with respect to the cavity and a fixing facility for fixing the insert piece in the cavity. According to the invention, the first insert element is fixed and sealed in the cavity of the housing in an operating state of the MPI phantom.

The inventive phantom has a removable insert element, whose depression can be filled with liquid or powder contrast medium and which can be sealed in a liquid-tight manner using the sealing element. In this way, the insert element can be simply filled with contrast medium and cleaned, and leakage or drying out can be prevented. Because the depression is sealed with respect to the cavity in the operating state, even if liquid contrast medium is used, the phantom can be oriented in any direction in the volume under examination of the imaging configuration. The inventive phantom is therefore easy to handle and is, in principle, suitable for all imaging methods even for those that use liquid or powder contrast medium (for example, MPI), which first have to be impressed with a "geometric structure" by the provision of suitable volumes that the contrast medium has to fill.

The insert element is plate-shaped (flat cuboid), i.e. the length and width (extent in the x/y direction in the operating state) are large compared with the height (extent in the z-direction in the operating state). In the operating state, the depression is open in the z-direction (upward). Preferably, the sealing element is also plate-shaped, so that a multiplicity of depressions in different configurations can be sealed. In this way, the sealing element can be used for different insert elements.

The purpose of the inventive phantom system is to check the spatial resolution and/or the image accuracy and/or the sensitivity and/or the susceptibility to artifacts of the imaging configuration.

In a special embodiment, the first insert element or at least the one depression of the first insert element is centered with respect to the central plane of the housing (the central plane is equidistant from the base of the depressions and from the opening of the depression). Therefore, if the housing is rotated about a rotary axis that extends through the center of the housing, the depressions of the insert element remain near to the center point of the housing, so that the risk that the depressions will move out of the FOV (field of view) is very small.

In a further variant of this embodiment, a compensation element is provided, which is constituted in such a way as to position the insert element in the z-direction within the housing. The compensation element functions as a spacer. The height of the compensation element depends on the height of the housing, the configuration of the cavity in the housing, the height of the insert element, and the depth of the depression, and is selected such that the depression in the z-direction is centered with respect to the housing when the compensation element and insert element are positioned in the housing. In addition, the height of the compensation element can be selected such that the insert element is disposed centered in the z-direction with respect to the housing when the compensation element and insert element are positioned in the housing, for example, when depressions of different depths are provided or when depressions are inserted in the insert element by the user him or herself.

Another embodiment comprises a second plate-shaped insert element with at least one depression for receiving a liquid substance, which, in the operating state, is fixed and sealed in the cavity of the housing. Furthermore, in this embodiment, the sealing facility has a second sealing element for the liquid-tight sealing of the second insert element with respect to the cavity.

In the operating state, the two insert elements or the depressions of the two insert elements are preferably disposed symmetrically with respect to the central plane of the housing. The depressions of the two insert elements are disposed symmetrically with respect to the central plane of the housing when the distance of the center points of the depressions with respect to the central plane of the housing is identical for the upper (first) and the lower (second) insert element. Insert elements filled with contrast medium are decisive for centering in the operating state. Additional elements with depressions located in the cavity, but which are not filled in the operating state, are not insert elements to be taken into account in the manner described above for the symmetrical configuration.

The housing of the inventive phantom system is preferably cuboidal, wherein the dimensions of the housing are chosen such that at least the one depression is positioned in the FOV in each orientation of the phantom in the measuring position within the imaging configuration. In particular, the length and the width of the housing should not be more than 1.55 times the height (extent in the z-direction) of the housing. It is especially advantageous if the housing is cubic. "Cubic" for the purpose of the invention is a body, which essentially has the same dimensions in all three spatial directions, wherein wall surfaces facing each other are mutually parallel and wall surfaces not facing each other are mutually orthogonal. Corners and/or edges can be beveled without losing the characteristic of being "cubic." Due to the inventive cubic structure, the phantom can always be aligned centrally in the magnet bore of the MPI configuration or of another imaging configuration in three spatial directions (x,y,z). This is advantageous, in particular, for MPI measurements because, for certain typical MPI implementations, the gradient strengths along the different spatial directions are generally different, which results in anisotropic resolution.

In a preferred embodiment, the fixing facility comprises a closing plate and detachable fastening means. In order to measure the phantom, the insert element is mechanically connected to the housing using the fastening means and sealed liquid-tight against the cavity. Consequently, the phantom can be positioned in any orientation within the imaging configuration. The insert element is preferably screwed to the housing. The same screw connection can be used to fix the compensation element and the sealing elements in position.

In a preferred embodiment, a positioning device for reproducible positioning relative to the housing of the at least one insert element is provided. The positioning device could be the fastening means of the fixing facility, for example. In addition, the insert element preferably has through-recesses (through-holes) through which the fastening means can be passed. Furthermore, it is advantageous if the compensation element also has recesses for passing through fastening means, wherein the recesses of the compensation element and of the insert element are coextensive in the operating state.

It is especially advantageous if the dimensions of the cavity and of at least one insert piece are so well matched that at least one insert piece can be positioned so that it is form-locked in the cavity. The insert element can therefore be placed in the cavity so that it fits exactly (without play). This can be achieved, for example, if the base of the insert element corresponds to the cross section of the cavity. The bases of the compensation element and of the insert element are preferably identical. Thus, the insert element can be placed in the cavity in a reproducible way. It is then possible to dispense with a positioning device. To ensure the correct orientation of the insert element, it is advantageous if the cross sections of the cavity and of the insert elements are such that the insert element can only be introduced into the cavity in a particular orientation (for example, different shaping of the corners).

It is particularly advantageous if the edges of the housing are beveled. By beveling (chamfering) the edges, the periphery of the phantom can be minimized without having to reduce the cavity of the housing. This permits easy insertion and positioning in bores of the magnet of the MPI configuration which are sometimes narrow (for example, a 48-mm scanner bore).

It is particularly advantageous if the insert elements are at least partially made of Polytetrafluoroethylene. For example, the depressions can be coated with a Polytetrafluoroethylene layer. In this way, evaporation and/or absorption of the solvent through the matrix and the resulting drying-up of the contrast medium liquid can be avoided so that the inventive phantom can be used for a longer period of time even with small quantities of contrast medium (a few µl), and thus different measuring series can be calibrated and/or characterized with the same phantom.

The MPI phantom system is preferably constituted for calibration and/or characterization of an MPI configuration and at least one further imaging configuration, in particular, an MRI configuration and/or a PET configuration and/or a µCT configuration. The MPI phantom is therefore preferably manufactured from a material that enables use of the phantom with different imaging methods. The preferred choice of material for the housing is transparent plastic, in particular, polymethyl methacrylate. This material is essentially transparent for the imaging methods, inert to solvents, and also has good sealing qualities.

In a special embodiment of the inventive phantom system, the cavity has a reservoir area and the sealing facility has a further sealing element, wherein, in the operating state, the further sealing element seals the reservoir area with respect to the insert area. The reservoir area is preferably disposed on the side of the cavity that is opposite the opening of the cavity (base of the pot-shaped lower part of the housing) and has a smaller cross section than the insert area. The reservoir area can, for example, be filled with water, in order to be able to supply a sufficiently large proton signal for performance calibration in an MRI configuration. To prevent contamination of the measuring apparatus with the contrast media, an external seal is preferably disposed between the cover part and the lower part of the housing in the operating state.

In a special embodiment of the inventive phantom system, the at least one depression of the insert element has a constant cross section in the z-direction (2D insert element).

The invention also concerns the use of a phantom system according to the claimed subject material for the characterization and/or calibration of an MPI configuration and at least one further imaging configuration, in particular, an MRI configuration and/or a PET configuration and/or a µCT configuration.

Furthermore, the invention concerns a configuration for an imaging method, in particular an MPI configuration, with a phantom system as described above, wherein the dimensions of the housing and of the at least one insert element are chosen such that at least one depression is positioned in the FOV in each orientation of the phantom in the measuring position within the imaging configuration.

The invention is shown in the drawing and is explained in more detail using various embodiments.

BRIEF DESCRIPTION OF THE DRAWING

FIGS. 4a-d show different insert elements of the inventive phantom system;

DESCRIPTION OF THE PREFERRED EMBODIMENT

Figure 1:
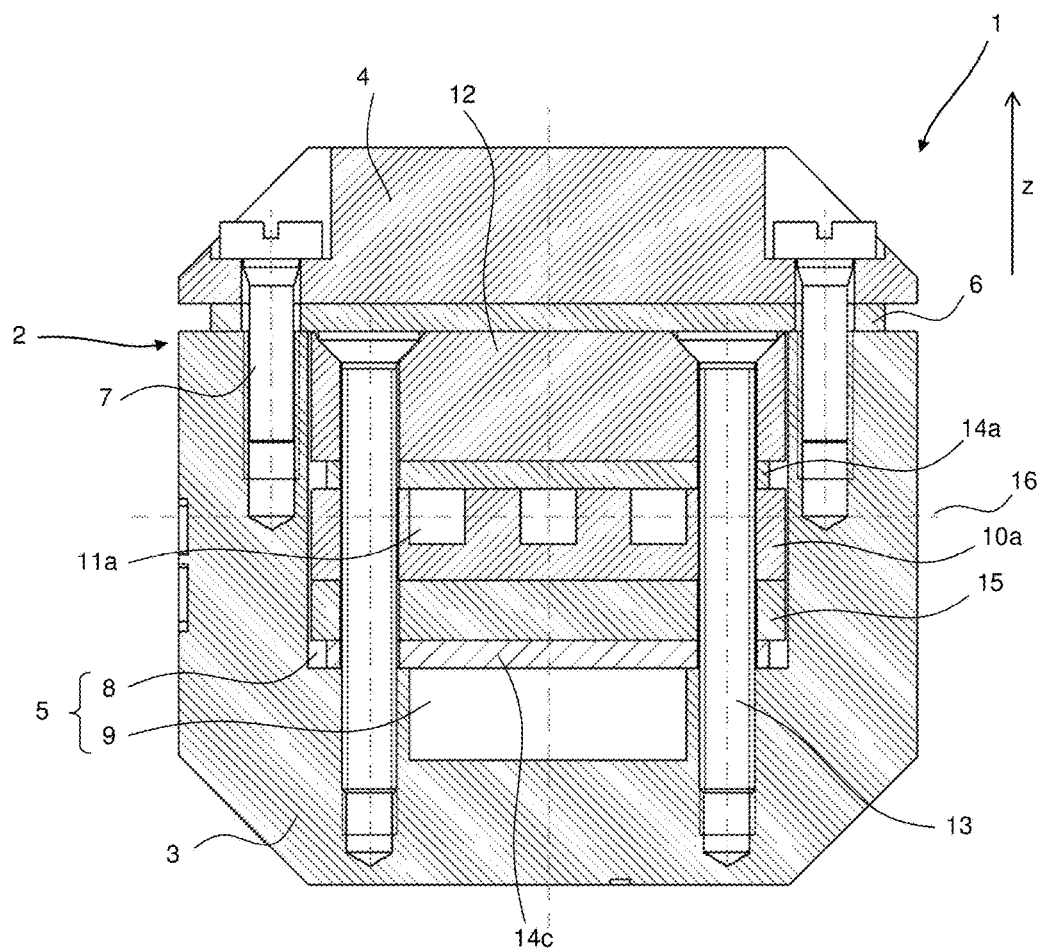
FIG. 1 shows a sectional view of an inventive phantom system with one insert element.
Figure 2:
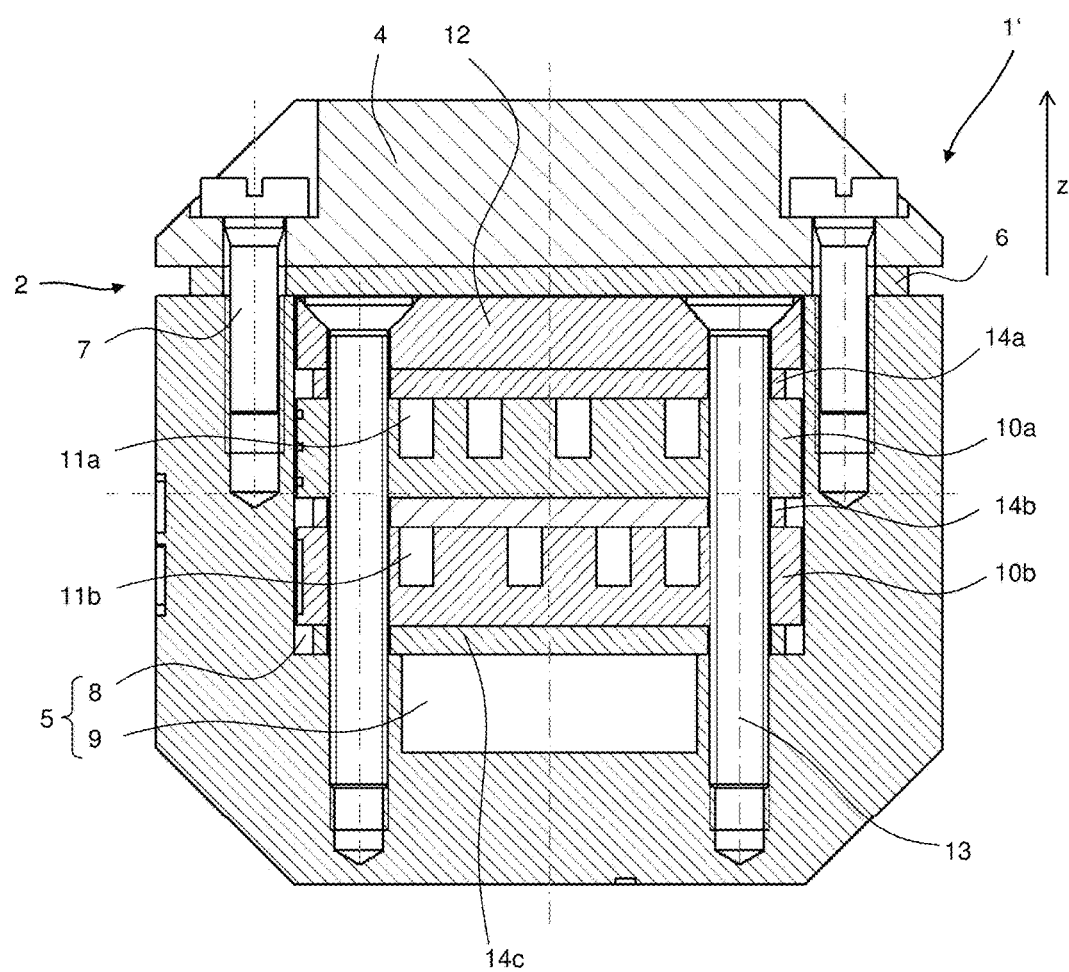
FIG. 2 shows a sectional view of an inventive phantom system with two insert elements.

FIGS. 1 and 2 show different embodiments 1, 1' of the inventive phantom system. Both embodiments 1, 1' comprise a housing 2. Housing 2 comprises a pot-shaped lower part 3 open to the top (z-direction) and a cover part 4 for closing the opening of housing 2, so that a cavity 5 is delimited by the lower part 3 and the cover part 4. The cavity 5 is sealed liquid-tight by means of an external seal 6. The lower part 3, the cover part 4, and the external seal 6 are detachably connected to each other by means of screws 7. The cavity 5 comprises an insert area 8 and a reservoir area 9. The insert area 8 is used to receive one or more insert elements 10a, 10b, which can be inserted into the cavity through the opening of the lower part 3. The insert elements 10a, 10b have depressions 11a, 11b into which contrast medium can be filled, and are fixed in the housing 2 via a closing plate 12 and a fastening means 13 (here: screws). The depressions 11 are sealed in a liquid-tight manner against the cavity 5 by means of first and second sealing elements 14a, 14b.

The reservoir area 9 has a smaller cross section than the insert area 8 and the insert elements 10a, 10b, so that there is no risk that the insert elements 10a, 10b will be mistakenly inserted into the reservoir area 9. The reservoir area 9 is used to receive water in order to be able to supply a sufficiently large proton signal for performance calibration in an MRI configuration, and is sealed liquid-tight against the insert area 8 by means of a further sealing element 14c. Because the reservoir area 9 has a smaller cross section than the insert area, the sealing element 14c can be constituted as a sealing mat, which is placed in cavity 5 on the reservoir area 9.

In the case of the embodiment shown in FIG. 1, only a first insert element 10a is disposed in cavity 5. By means of a compensation element 15 of suitable height (extent in the z-direction), the position of the insert element 10a can be adjusted in the z-direction in such a way that the center points of depressions 11 are located at the height of the central plane 16.

FIG. 2 shows an embodiment in which two insert elements 10a, 10b are disposed in the cavity 4. The height of the insert elements 10a, 10b, of the second sealing element 14b and of the further sealing element 14c are chosen such that the bases of the depressions 11a of the first insert element 10a and the upper edges of the depressions 11b of the second insert element are equidistant from the central plane 16. To use the sealing elements 14b, 14c and the insert elements 10a, 10b for housings with cavities of different heights, a compensation element can be used here, too, in order to dispose depressions 11a, 11b symmetrically with respect to the central plane 16.

Figure 3A:
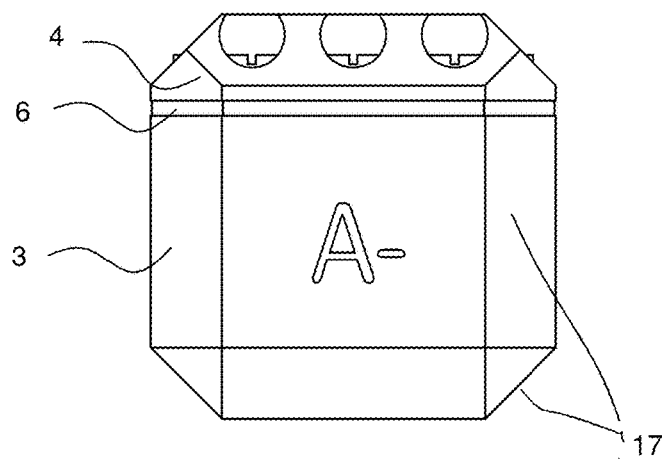
FIGS. 3a-c show a side view, front view, and view from above of an inventive phantom system.
Figure 3B:
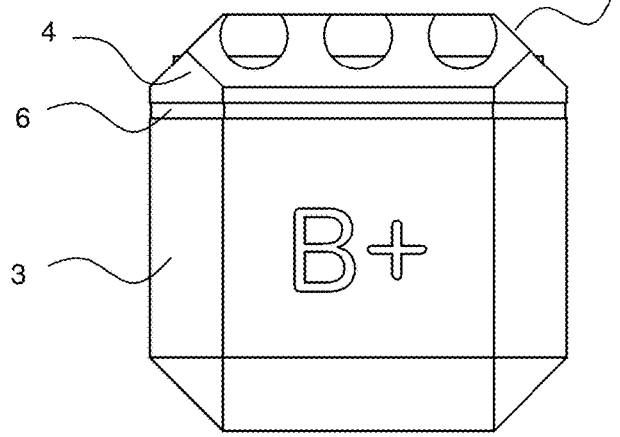
Figure 3C:
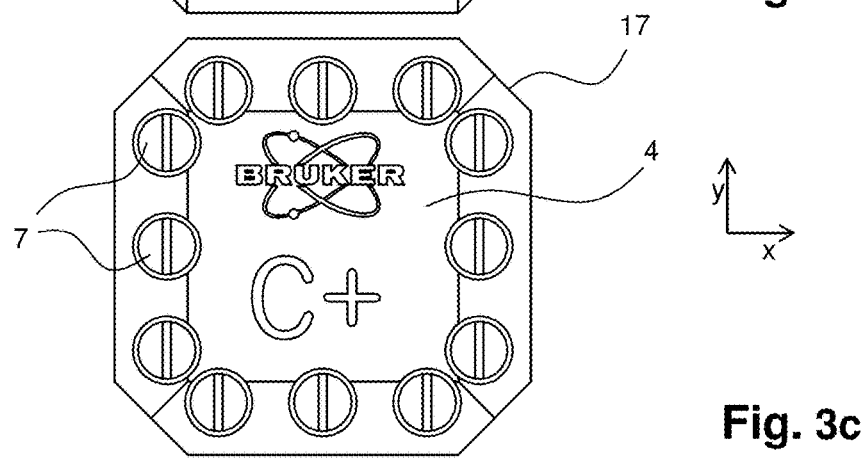

FIGS. 3a-c show outside views of the phantom system in the three spatial directions x, y, z. In the embodiment shown, the housing is cubic and has chamfered edges 17, so that it is easier to position the phantom system in what are sometimes narrow bores of magnets, for example, of an MPR or MRI configuration. The lateral surfaces of the housing are labeled with engraved lettering A+, A−, B+, B−, C+, C− to provide a simple way of specifying an allocation to the coordinate axes of the imaging configuration for each orientation.

FIGS. 4a-c show different insert elements of the inventive phantom system. The insert elements have an effective imaging cross section of D20×20 mm$^2$. Through-holes 18 are disposed at the edge of the insert elements, through which the fastening means 13 can be inserted in order to fix and position the insert element inside the housing. Different phantom structures are required to examine different aspects. For example, the spatial resolution can be examined by disposing small volumes of contrast medium at variable distances in order to verify in the image from which distance the structures are no longer resolved. For sensitivity examinations, a concentration series is placed in the phantom system.

FIG. 4a shows an insert element with which the resolution of the imaging system can be determined. For this, the insert element has 4×4 main depressions 11 with a diameter of 2 mm, which have variable spacing between them (1-3.5 mm in steps of 0.5 mm). Furthermore, additional depressions 11' are provided for a second contrast medium, so that the phantom system can be used in multiple imaging configurations without having to change the contrast medium. Constitution of an additional depression 11' as a concentric ring around a main depression 11 permits reliable superimposition of images from two modalities (imaging methods) even in cases where the first contrast medium in the depressions 11 is not visible in a second modality.

FIG. 4b shows an insert element with which, for example, the sensitivity of the imaging system can be determined. In the insert element shown in FIG. 4b, nine main depressions 11 are disposed equidistantly. Here, too, additional depressions 11' (here: ring-shaped) are provided. FIG. 4c shows an insert element in which the depressions are constituted as letters. FIG. 4d shows an insert element blank into which an individual configuration of depressions can be introduced.

Figure 5A:
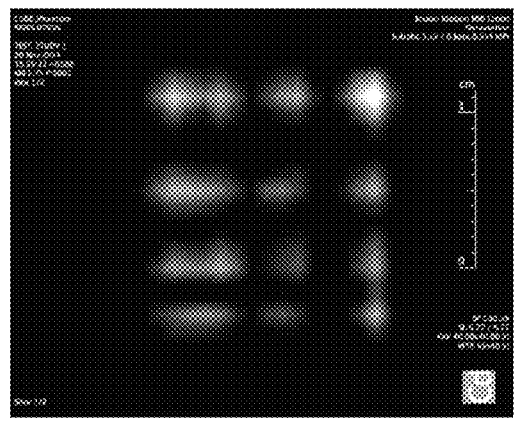
FIG. 5a shows an MPI image acquired with an inventive phantom system.
Figure 5B:
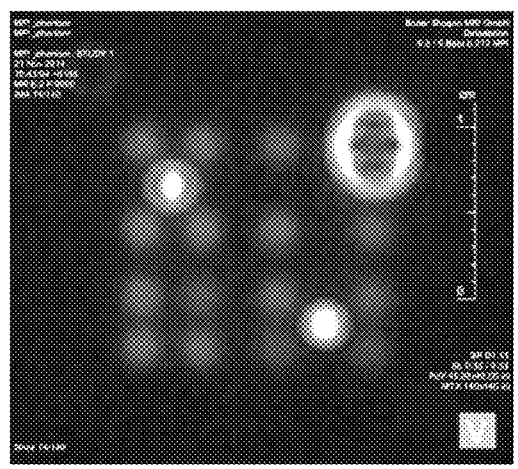
FIG. 5b shows an MRI image acquired with an inventive phantom system.
Figure 5C:
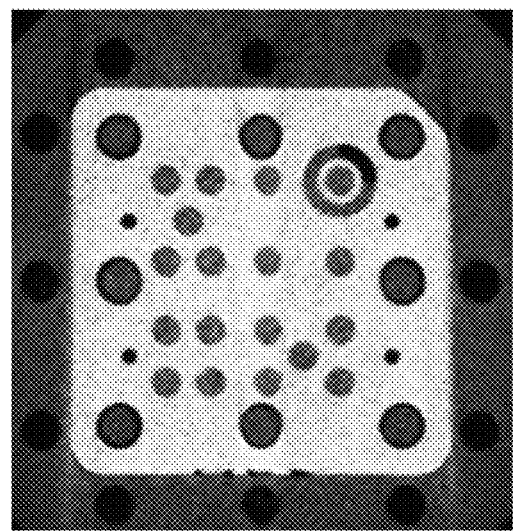
FIG. 5c shows an µCT image acquired with an inventive phantom system.

FIGS. 5a-c show images of the insert element from FIG. 4a acquired with an inventive phantom system, wherein the main depressions 10 are filled with an MPI contrast medium (LS-7, LodeSpin Labs) and the additional depressions 10' are filled with $Cu^{2+}$-doped water for MRI acquisitions. An MPI image (FIG. 5a) was acquired with a Bruker MRI/MPI hybrid system, an MRI image (FIG. 5b) with a Bruker BioSpec 94/30 MRI system, and a μCT image (FIG. 5c) with a Bruker SkyScan 1176 μCT system. In all images, good contrast between the contrast media and the insert element can be seen.

LIST OF REFERENCE SYMBOLS 1, 1' Phantom system
2 Housing
3 Lower part
4 Cover part
5 Cavity
6 External seal
7 Screws for fixing the cover part on the lower part of the housing
8 Insert area of the cavity
9 Reservoir area
10a First insert element
10b Second insert element
11a, Depression in first insert element
11b Depression in second insert element
11 Main depression
11' Additional depression
12 Closing plate
13 Fastening means
14a First sealing element
14b Second sealing element
14c Further sealing element
15 Compensation element
16 Central plane
17 Beveled edges
18 Through-hole in insert element

We claim:

1. A phantom system for calibration and/or characterization of an imaging configuration, the phantom system comprising:
    a housing, said housing comprising a lower part having an opening in a z-direction and a cover part for closing said opening of said housing, wherein said lower part and said cover part delimit a cavity having an insert area;
    a first plate-shaped insert element having at least one depression for receiving a liquid substance, said first plate-shaped insert element structured for placement within said cavity;
    a sealing facility having a first sealing element for liquid-tight sealing of said first plate-shaped insert element with respect to said cavity; and
    a fixing facility for fixing said first plate-shaped insert element in said cavity, wherein said first plate-shaped insert element is fixed and sealed in said cavity of said housing in an operating state of the phantom, wherein said fixing facility comprises a closing plate and detachable fastening means.

2. The phantom system of claim 1, wherein said first insert element or said at least one depression of said first insert element is disposed centrally with respect to a central plane of said housing.

3. The phantom system of claim 2, further comprising a compensation element, which is constituted in such a way as to position said first insert element in the z-direction inside said housing.

4. The phantom system of claim 1, further comprising a second plate-shaped insert element having at least one depression for receiving a liquid or powder substance, wherein, in said operating state, said second plate-shaped insert element is fixed and sealed in said cavity of the housing, said sealing facility further comprising a second sealing element for liquid-tight sealing of said second insert element against said cavity.

5. The phantom system of claim 4, wherein, in said operating state, said first and said second insert elements or depressions in said first and said second insert elements are disposed symmetrically with respect to a central plane of said housing.

6. The phantom system of claim 1, wherein the phantom system comprises a positioning device for reproducible positioning of said first insert element relative to said housing.

7. The phantom system of claim 1, wherein edges of said housing are chamfered.

8. The phantom system of claim 1, wherein said first insert element is at least partially made of Polytetrafluoroethylene.

9. The phantom system of claim 1, wherein the phantom system is suitable for characterization and/or calibration of an MPI configuration and at least one of an MRI configuration, a PET configuration and a μCT configuration.

10. The phantom system of claim 9, wherein said cavity has a reservoir area and said sealing facility has a further sealing element, wherein, in said operating state, said further sealing element seals said reservoir area against said insert area.

11. The phantom system of claim 1, further comprising an external seal, wherein, in said operating state, said external seal is disposed between said cover part and said lower part of said housing.

12. A method for imaging, the method comprising the step of calibrating and/or characterizing an MPI configuration and at least one of an MRI configuration, a PET configuration and a μCT configuration using the phantom system of claim 1.

13. A configuration or an MPI configuration for an imaging method, the configuration comprising the phantom system of claim 1, wherein said housing and said first insert element are disposed, structured and dimensioned such that at least one depression is positioned in a FOV in each orientation of the phantom system in a measuring position within an imaging configuration.

* * * * *